(12) United States Patent
Hu et al.

(10) Patent No.: US 10,512,755 B2
(45) Date of Patent: Dec. 24, 2019

(54) SEPTUM SECUREMENT

(71) Applicant: Becton, Dickinson and Company, Franklin Lakes, NJ (US)

(72) Inventors: YingYong Hu, Singapore (SG); Kiat Jin Cheng, Singapore (SG); Yun Hui Wong, Singapore (SG); S. Ray Isaacson, Layton, UT (US)

(73) Assignee: Becton, Dickinson and Company, Franklin Lake, NJ (US)

( * ) Notice: Subject to any disclaimer, the term of this patent is extended or adjusted under 35 U.S.C. 154(b) by 125 days.

(21) Appl. No.: 15/617,646

(22) Filed: Jun. 8, 2017

(65) Prior Publication Data
US 2018/0353729 A1    Dec. 13, 2018

(51) Int. Cl.
*A61M 5/178* (2006.01)
*A61M 25/00* (2006.01)
*A61M 25/06* (2006.01)
*A61M 39/06* (2006.01)
*A61M 39/00* (2006.01)

(52) U.S. Cl.
CPC .... *A61M 25/0075* (2013.01); *A61M 25/0097* (2013.01); *A61M 25/065* (2013.01); *A61M 25/0606* (2013.01); *A61M 39/06* (2013.01); *A61M 2025/0076* (2013.01); *A61M 2039/0072* (2013.01); *A61M 2039/066* (2013.01)

(58) Field of Classification Search
CPC ...... A61M 2039/0072; A61M 25/0075; A61M 25/0097; A61M 25/065; A61M 25/0606; A61M 39/06; A61M 36/04; A61M 5/158
See application file for complete search history.

(56) References Cited

U.S. PATENT DOCUMENTS

| 7,678,101 B2 * | 3/2010 | Sage ................. A61M 39/1011 604/533 |
| 2013/0165867 A1 | 6/2013 | Isaacson et al. |
| 2014/0364809 A1 | 12/2014 | Isaacson et al. |
| 2015/0151088 A1 | 6/2015 | Lim et al. |

FOREIGN PATENT DOCUMENTS

| WO | 02/096495 | 12/2002 |
| WO | 2007/050788 | 5/2007 |

* cited by examiner

*Primary Examiner* — Rebecca E Eisenberg
(74) *Attorney, Agent, or Firm* — Kirton & McConkie; Craig Metcalf; Kevin Stinger

(57) ABSTRACT

A catheter assembly may include a catheter adapter, which may include a proximal end, a distal end, and a lumen extending between the proximal end and the distal end. The distal end may include a catheter configured to be inserted into vasculature of a patient. The catheter assembly may also include a septum, which may be disposed within the lumen of the catheter adapter. The septum may be secured within the lumen in response to increased pressure by one or more of the following: one or more septum stoppers, a retention disc of a needle assembly, a U-shaped washer, and a conical washer.

5 Claims, 13 Drawing Sheets

SEPTUM SECUREMENT

BACKGROUND OF THE INVENTION

Once placement of an introducer needle within a blood vessel of a patient has been confirmed, a clinician may temporarily occlude flow in the blood vessel and remove the introducer needle, leaving a catheter in place within the blood vessel. The clinician may also attach a device to the catheter for fluid infusion and/or blood withdrawal. This process has been somewhat difficult in practice since many catheter placement sites simply do not allow easy occlusion of the blood vessel. Additionally, even when such occlusion is achieved, it may be imperfect, resulting in blood leaking from a catheter assembly housing the catheter and endangering medical personnel.

Catheter assemblies have thus been provided in the art that provide a variety of seals or "septa" for preventing outflow of fluid during and following removal of the introducer needle from the blood vessel. A septum may be secured within the catheter assembly via friction and/or adhesive between the septum and a wall of the catheter assembly. However, in some instances, septum dislodgement may occur in response to pressurization of the catheter assembly, which may result from venous pressure, fluid injection under high or low pressure, flush of the catheter assembly, blood collection, etc. Septum dislodgement presents a risk of exposure by medical personnel to blood or other fluids. Accordingly, there is a need in the art for devices, systems, and methods that provide securement of the septum.

BRIEF SUMMARY OF THE INVENTION

The present disclosure may relate generally to devices, systems, and associated methods to stabilize or secure a septum. In some embodiments, the catheter assembly may include a catheter adapter, which may include a proximal end, a distal end, and a lumen extending between the proximal end and the distal end. In some embodiments, the distal end may include a catheter configured to be inserted into vasculature of the patient.

In some embodiments, the catheter assembly may include the septum, which may be disposed within the lumen. In some embodiments, the catheter assembly may include a septum securement element that may be disposed proximate the septum and/or proximal to a distal end of the septum. In some embodiments, the septum securement element may be configured to secure the septum in response to a proximal force on the septum. In some embodiments, the septum securement element may include one or more of the following: one or more septum stoppers, a retention disc of a needle assembly, a sharp element, a U-shaped washer, and a conical washer.

In some embodiments, the septum may include one or more grooves. In some embodiments, the catheter assembly may include the one or more septum stoppers. In some embodiments, each of the septum stoppers may extend through a wall of the catheter adapter and into the grooves of the septum. In some embodiments, the grooves may include an adhesive.

In some embodiments, each of the septum stoppers may include a cylindrical bottom portion and a head. In some embodiments, the head may have a greater diameter than the cylindrical bottom portion. In some embodiments, a top surface of the head may be rounded. In some embodiments, each of the septum stoppers may extend through a stopper hole in the wall of the catheter adapter. In some embodiments, the stopper hole may include an outer portion having a shape corresponding to the head and an inner portion having a shape corresponding to the cylindrical bottom portion.

In some embodiments, the septum stoppers may include a first septum stopper and a second septum stopper. In some embodiments, the first septum stopper and the second septum stopper may be aligned with or oppose each other. In these and other embodiments, the first septum stopper and the second septum stopper may be disposed on opposite sides of the septum, which may facilitate retention of the septum. In some embodiments, the septum may include a single annular groove.

In some embodiments, the catheter assembly may include an introducer needle, which may extend through the catheter adapter. In some embodiments, the catheter assembly may include a washer disposed within the lumen and proximal to the septum. In some embodiments, the washer may include two arms spaced apart and forming a U-shape. In some embodiments, ends of each of the arms may be disposed within a groove or hole in the catheter adapter. In some embodiments, the introducer needle may extend between the two arms.

In some embodiments, another washer may be disposed within the lumen and proximal to the septum. In some embodiments, the other washer may have a conical-shape. In some embodiments, in response to a force on the septum in a proximal direction, the conical shape may compress and the washer may exert a greater force on the wall of the catheter adapter. In some embodiments, the other washer may be resilient such that in response to removal of the force on the septum in the proximal direction, the other washer may return to the conical shape.

In some embodiments, the washer may include an inner margin and/or an outer margin. In some embodiments, the outer margin may contact the wall of the catheter adapter. In some embodiments, an entirety of the outer margin may contact the wall of the catheter adapter. In some embodiments, the inner margin may include one or more outward-extending slots. In some embodiments, the outer margin may include one or more inward-extending slots. In some embodiments, the inner margin may be an inner circumference. In some embodiments, the outer margin may be an outer circumference. In some embodiments, the inner margin may form an opening through which the introducer needle may extend.

In some embodiments, the catheter assembly may include a needle assembly, which may be coupled to the catheter adapter. In some embodiments, a distal end of the needle assembly may include one or more arms and a retention disc coupled to the one or more arms. In some embodiments, the retention disc may be secured within the lumen proximal to the septum. In some embodiments, each of the arms may include a line of weakness. In some embodiments, in response to twisting a proximal end of the needle assembly with respect to the catheter adapter, each of the arms may be configured to break at the line of weakness, the retention disc may be secured within the catheter adapter, and the proximal end of the needle assembly may be uncoupled from the catheter adapter. In some embodiments, the line of weakness includes an indented portion.

In some embodiments, the retention disc may include one or more wings. In some embodiments, the wall of the catheter adapter may include one or more grooves or slots that may be configured to engage the wings in a snap-fit. In some embodiments, the retention disc and the wall include corresponding threads. In some embodiments, the retention disc is ring-shaped and/or includes an opening through which the introducer needle may extend.

BRIEF DESCRIPTION OF THE SEVERAL VIEWS OF THE FIGURES

In order that the manner in which the above-recited and other features and advantages of the invention will be readily understood, a more particular description of the devices, systems, and associated methods to secure a septum briefly described above will be rendered by reference to specific embodiments thereof, which are illustrated in FIGS. 1-4. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

Figure 1A:
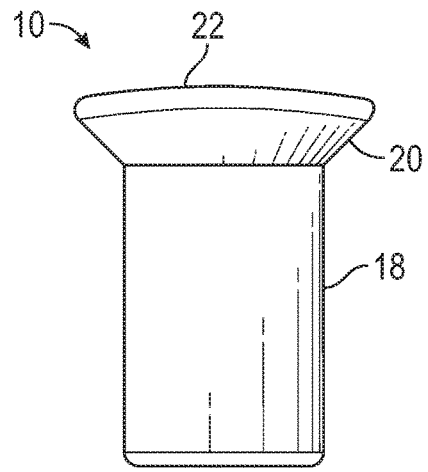
FIG. 1A is a side view of an example septum stopper, according to some embodiments.
Figure 1B:
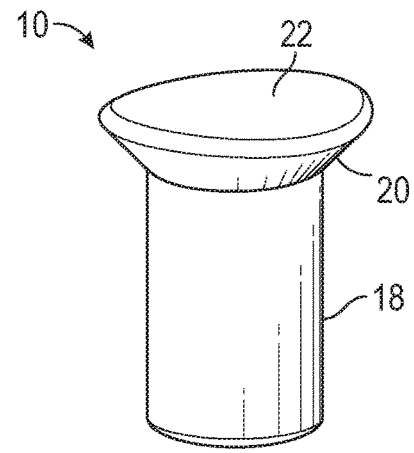
FIG. 1B is an upper perspective view of the septum stopper of FIG. 1A, according to some embodiments.

It will be readily understood that the components of the present invention, as generally described and illustrated in the Figures in the present disclosure, could be arranged and designed in a wide variety of different configurations. Thus, the following more detailed description of the embodiments, represented in FIGS. 1-4, is not intended to limit the scope of the invention, as claimed, but is merely representative of some embodiments of the invention.

Referring now to FIGS. 1A-1F, in some embodiments, one or more septum stoppers 10 may help secure a septum 12 within a catheter adapter 14 of a catheter assembly 16. In some embodiments, the septum 12 may include a blood control septum. The septum stoppers 10 may include a variety of shapes and sizes. In some embodiments, each of the septum stoppers 10 may include a cylindrical bottom portion 18 and/or a head 20 protruding outwardly from the bottom portion 18.

In some embodiments, each of the septum stoppers 10 may include a rounded top surface 22. For example, each of the septum stoppers 10 may include a convex or concave top surface 22. In some embodiments, the rounded top surface 22 may match a curvature of an outer surface of the catheter adapter 14 such that there is a smooth transition between the outer surface of the catheter adapter 15 and each of the septum stoppers 10. FIGS. 1D-1E illustrate the catheter assembly 16 in an insertion configuration, with an introducer needle 40 extending through the catheter adapter 14 and beyond a distal end of a catheter 42.

In some embodiments, the septum 12 may include one or more grooves 24. In some embodiments, the grooves 24 may be annular. In some embodiments, the grooves 24 may be aligned with one or more slots or stopper holes 26 that extend through a wall 28 of the catheter adapter 14. In some embodiments, each of the stopper holes 26 may be sized and configured to secure a particular septum stopper 10. For example, each of the stopper holes 26 may include an inner portion corresponding to a size and shape of the bottom portion 18 and/or an outer portion corresponding to a size and shape of the head 20.

In some embodiments, the septum stoppers 10 may extend through the stopper holes 26 such that ends of each of the septum stopper 10 are disposed in the grooves 24, securing the septum 12 within the catheter adapter 14. In some embodiments, to further secure the septum stoppers 10 within the stopper holes 26 and/or the grooves 24, an adhesive 29 may be applied to one or more of the following: the stopper holes 26, the septum stoppers 10, and the grooves 24.

Figure 1C:
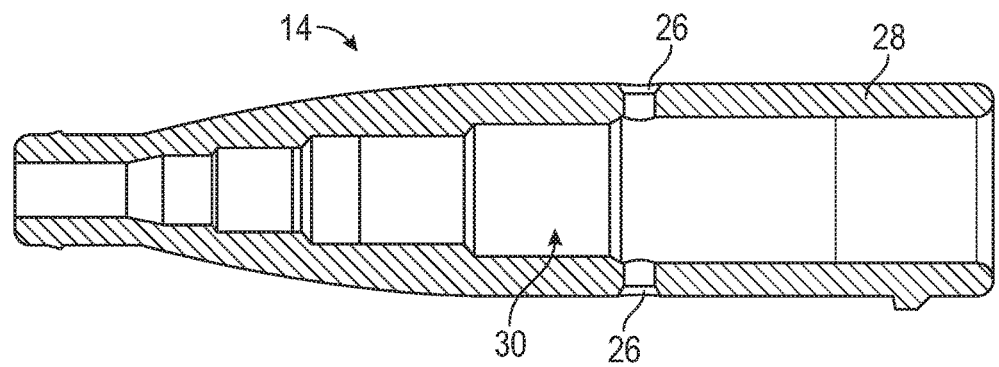
FIG. 1C is a cross-section side view of an example catheter adapter, according to some embodiments.
Figure 1D:
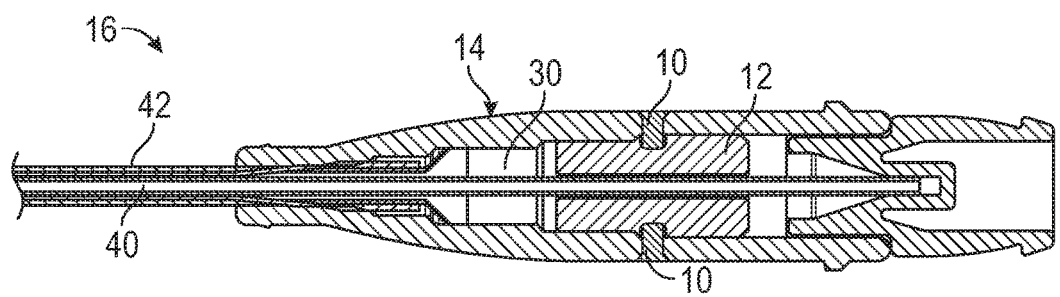
FIG. 1D is a cross-sectional side view of an example catheter assembly, illustrating multiple of the septum stoppers of FIG. 1A securing an example septum within the catheter adapter of FIG. 1C, according to some embodiments.
Figure 1E:
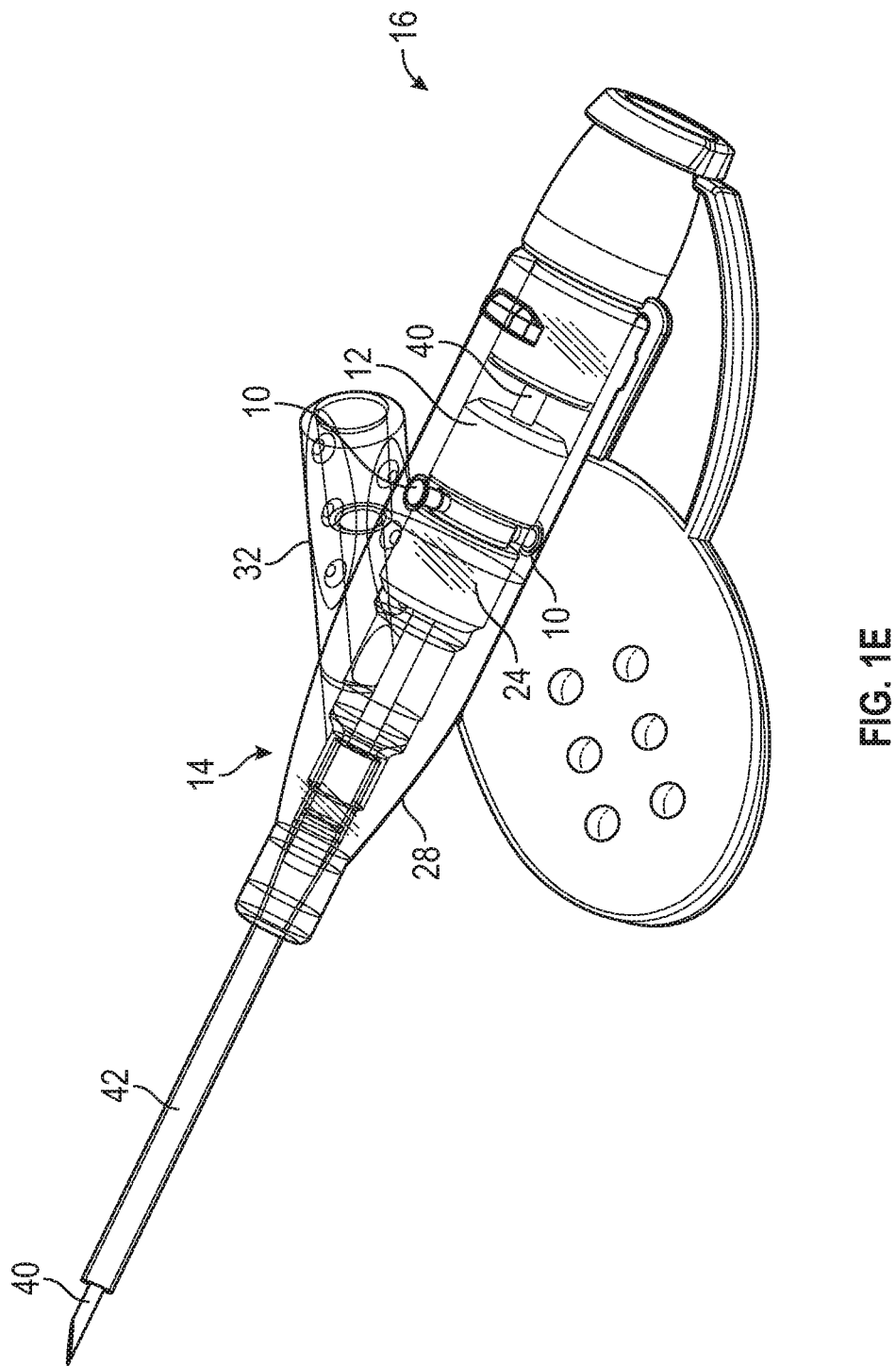
FIG. 1E is a lower perspective view of the catheter assembly of FIG. 1D, according to some embodiments.

In some embodiments, the catheter adapter 14 may include a first stopper hole 26 and a second stopper hole 26, as illustrated in FIG. 1C, for example. In some embodiments, the first stopper hole 26 and the second stopper hole 26 may be opposing and disposed on opposite sides of the catheter adapter 14. However, the catheter assembly 16 may include any number of septum stoppers 10 and corresponding stopper holes 26. For example, the catheter adapter 14 may include three or four stopper holes 26 and septum stoppers 10. In some embodiments, the stopper holes 26 may be spaced around a circumference of the catheter adapter 14 and/or aligned with a single annular groove 24. In some embodiments, the stopper holes 26 may be disposed at any location around the septum 12.

In some embodiments, the septum 12 may be integrally formed. In some embodiments, the septum 12 may include multiple pieces or components. In some embodiments, a particular groove 24 may be formed at an intersection of the components. Suitable materials for the septum stoppers 10 and/or the catheter adapter 14 may include, but are not limited to, thermoplastic polymeric resins such as polycarbonate, polystyrene, polypropylene, polycarbonate, polyethylene terephthalate glycol (PETG), copolyester, and the like. Suitable materials for the septum stoppers 10 and/or the catheter adapter 14 may include, but are not limited to, metals such as steel, zinc, nickel, silver, and the like.

Figure 1F:
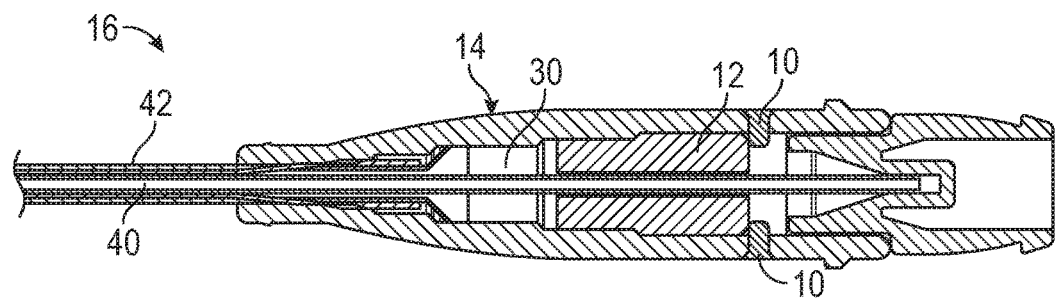
FIG. 1F is a cross-sectional side view of the catheter assembly of FIG. 1D, according to some embodiments.

In some embodiments, during assembly of the catheter assembly 16, the septum 12 may be placed within a lumen 30 of the catheter adapter 14 such that grooves 24 of the septum 12 are aligned with the stopper holes 26 extending through the wall 28 of the catheter adapter 14. In some embodiments, the septum stoppers 10 may then be placed within the stopper holes 26, the ends of the septum stoppers 10 fitting securely within the grooves 24 to secure the septum 12 to the catheter adapter 14. Additionally or alternatively, in some embodiments, one or more stopper holes 26 may be disposed proximal to the septum 12, and the septum stoppers 10 disposed within the stopper holes 26 may extend into the lumen 30 proximate the proximal end of the septum 12, as illustrated in FIG. 1F. In some embodiments, the septum stoppers 10 may contact or be slightly spaced apart from the proximal end of the septum 12.

In some embodiments, when the catheter assembly 16 is pressurized or when fluid is infused into the catheter adapter 14 at a high pressure, such as, for example, via a power injector through a port 32, the septum stoppers 10 may prevent the septum 12 from being dislodged from the catheter adapter 14. In some embodiments, the high pressure may be 300 psi or greater.

In some embodiments, the catheter assembly may include an intravenous (IV) catheter. In some embodiments, the catheter assembly 16 may be integrated or non-integrated. It is understood that the septum stoppers 10 may be used in various types of catheter assemblies, vascular access devices, and with various types of septa. In some embodiments, the catheter assembly 16 may correspond to the BD INTIMA II™ IV Catheter, the BD NEXIVA™ DIFFUSICS™ Closed IV Catheter System, or another catheter assembly.

Figure 2A:
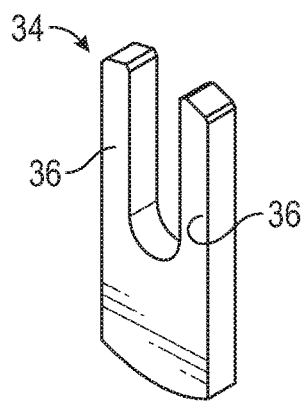
FIG. 2A is an upper perspective view of an example washer, according to some embodiments.

Referring now to FIG. 2A, additionally or alternatively to the septum stoppers 10, in some embodiments, a catheter assembly 33 may include a clip or washer 34 to secure the septum 12. In some embodiments, the catheter assembly 33 may include or correspond to the catheter assembly 16 of FIG. 1. In some embodiments, the washer 34 may be U-shaped. In some embodiments, arms 36 of the washer 34 may be generally parallel to each other. Suitable materials for the washer 34 and/or the catheter adapter 14 may include, but are not limited to, thermoplastic polymeric resins such as polycarbonate, polystyrene, polypropylene, polycarbonate, polyethylene terephthalate glycol (PETG), copolyester, and the like. Suitable materials for the washer 34 and/or the catheter adapter 14 may include, but are not limited to, metals such as steel, zinc, nickel, silver, and the like.

Figure 2B:
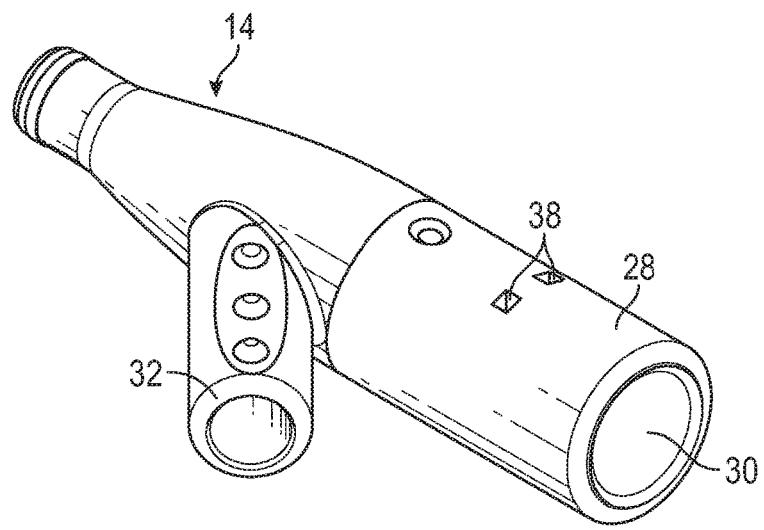
FIG. 2B is an upper perspective view of the catheter adapter of FIG. 1C, illustrating example holes for retaining the washer of FIG. 2A, according to some embodiments.

Referring now to FIG. 2B, in some embodiments, the catheter adapter 14 may include two holes 38, which may extend through the wall 28 of the catheter adapter 14. In some embodiments, each of the holes 38 may be sized and configured to receive an end of a particular arm 36 of the washer 34. As an alternative to the two holes 38, in some embodiments, an inner wall forming the lumen 30 of the catheter adapter may include two grooves, which may each be sized and configured to receive the end of the particular arm 36 of the washer 34. In some embodiments, to further secure the ends of the arms 36 within the holes 38 or grooves, the adhesive 29 may be applied to one or more of the ends of the arms 36 and/or the holes 38 or grooves.

Figure 2C:
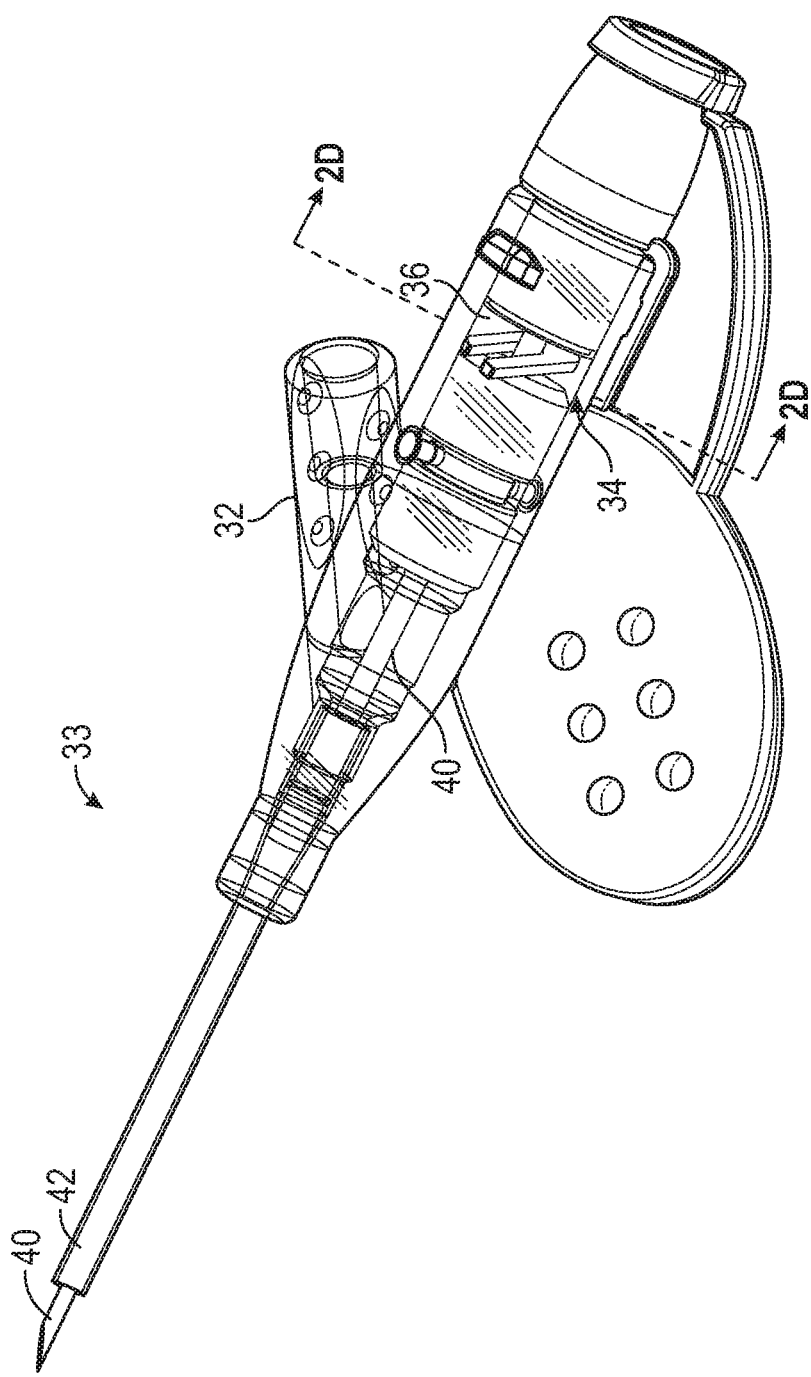
FIG. 2C is an upper perspective view of another catheter assembly, illustrating the washer of FIG. 2A and the holes of FIG. 2B, according to some embodiments.
Figure 2D:
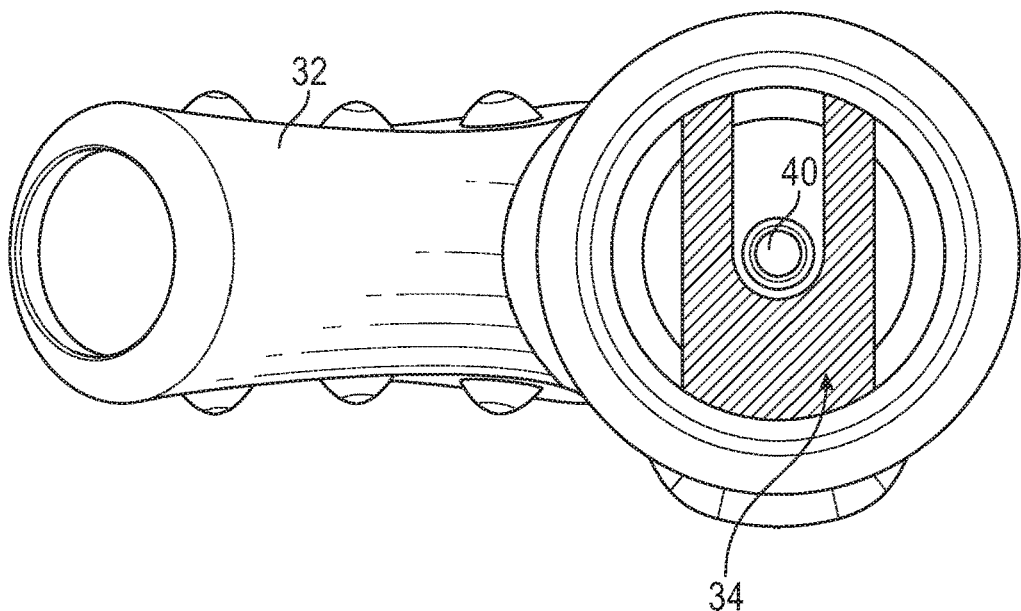
FIG. 2D is a cross-sectional side view of the catheter assembly of FIG. 2C, across line 2D-2D of FIG. 2C, according to some embodiments.

Referring now to FIGS. 2C-2D, in some embodiments, the washer 34 may be disposed within the lumen 30 of the catheter adapter 14 proximal to the proximal end of the septum 12. In some embodiments, the washer 34 may be disposed within the lumen 30 of the catheter adapter 14 in contact with the proximal end of the septum 12 or spaced apart from the proximal end of the septum 12. In some embodiments, the washer 34 may contact and/or apply pressure to the proximal end of the septum 12 in response to the septum 12 being forced proximally, which may occur in response to pressurization, such as, for example, infusion of fluid at the high pressure.

In some embodiments, when the catheter assembly 33 is in an insertion configuration ready to be inserted into vasculature of a patient, as illustrated in FIG. 2C, the introducer needle 40 may extend through a central portion of the washer 34, between the two arms 36. As illustrated in FIG. 2D, in some embodiments, the needle 40 may be spaced apart from the washer 34 when the needle 40 extends through the central portion of the washer 34. In some embodiments, when the catheter assembly 33 is in the insertion configuration, the needle 40 may also extend through the septum 12 and extend from a distal end of the catheter 42 coupled to the catheter adapter 14.

In some embodiments, when the catheter 42 is placed within the vasculature, the catheter assembly 33 may be moved to a fluid delivery configuration in which the needle 40 is retracted, and fluid may be delivered to the vasculature of the patient through the catheter 42. In some embodiments, the power injector may be coupled to the port 32, and fluid may flow into the catheter adapter 14 via the port 32. In some embodiments, the arms 36 of the washer 34 may be disposed in the holes 38 and the washer 34 secured within the lumen 30 in both the fluid delivery configuration and the insertion configuration.

Figure 2E:
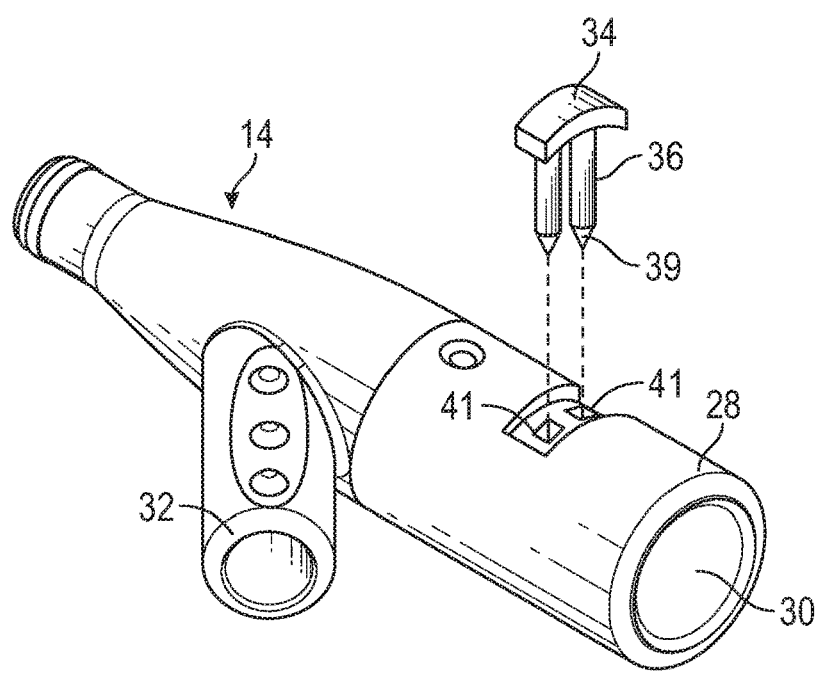
FIG. 2E is an upper perspective view of the washer of FIG. 2A, according to some embodiments.
Figure 2F:
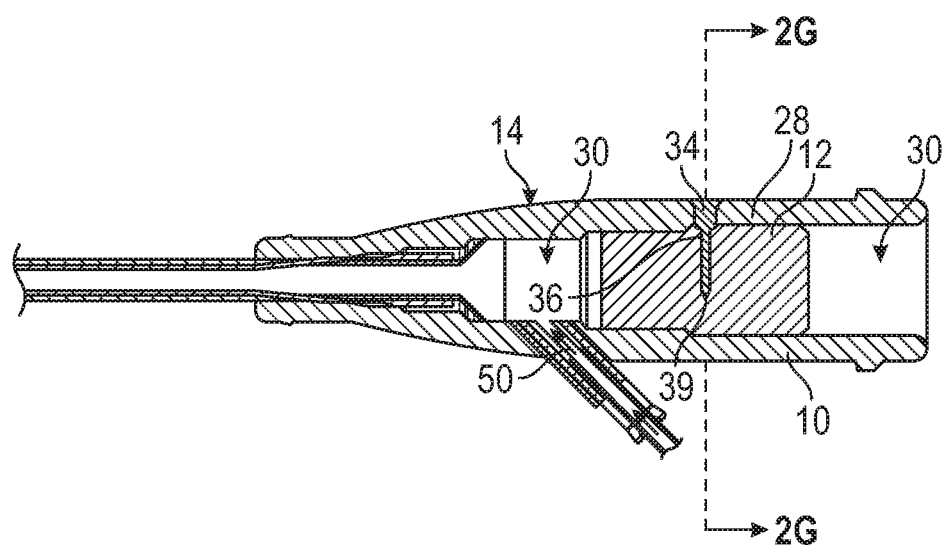
FIG. 2F is a cross-sectional side view of the catheter assembly of FIG. 1C, according to some embodiments.
Figure 2G:
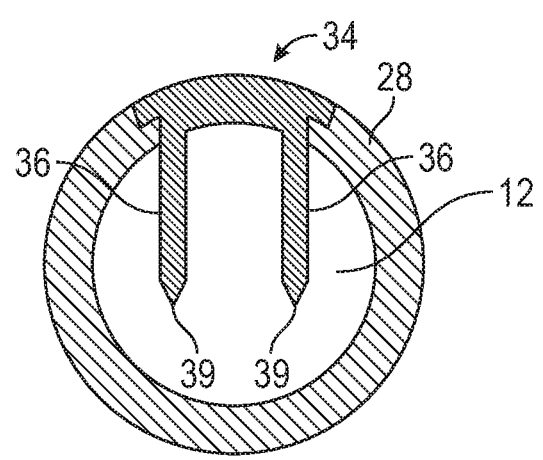
FIG. 2G is a cross-sectional view across line 2G-2G of FIG. 2F, according to some embodiments.

Referring now to FIGS. 2E-2G, in some embodiments, one or more of the arms 36 of the washer 34 may terminate in a pointed or sharp element 39 that may pierce the septum 12 to facilitate securement of the septum 12. In some embodiments, the sharp elements 39 may be pin-shaped, as illustrated in FIG. 2A. In some embodiments, the sharp elements 39 may be configured to pierce the septum 12 to secure the washer 34 to the septum 12. In some embodiments, the sharp elements 39 may allow the septum 12 to be placed less accurately, because the sharp elements 39 may be disposed at various points along a length of the septum 12 and still secure the septum 12 at the high pressure. In some embodiments, the septum 12 may be constructed of a resilient, flexible material, which may facilitate piercing of the septum 12 by the sharp elements 39. For example, the septum 12 may be constructed of silicon, polyisoprene, rubber, an elastomeric polymer, or another material. In some embodiments, the wall 28 of the catheter adapter 14 may include one or more apertures 41 that allow insertion of the washer 34 into the septum 12. In some embodiments, a curvature of an outer portion of the washer 34 may match a curvature of an outer surface of the wall 34 such that a smooth transition is provided across an outer surface of the catheter adapter 14.

Referring now to FIGS. 3A-3D, additionally or alternatively to the septum stoppers 10, in some embodiments, a catheter assembly 43 may include another type of washer 44 to secure the septum 12. In some embodiments, the catheter assembly 43 may include or correspond to the catheter assembly 16 of FIG. 1 and/or the catheter assembly 33 of FIG. 2. In some embodiments, the washer 44 may be positioned within the lumen 30 of the catheter adapter 14 proximal to the septum 12. In some embodiments, the washer 44 may be conical or domed-shaped in a relaxed state. In these and other embodiments, an inner circumference or inner margin 46 of the washer may be distal to an outer circumference or outer margin 48 of the washer 44.

In some embodiments, the washer 44 may be disposed in the relaxed state prior to pressure being applied to the septum 12, such as, for example, through infusion of fluid 50 into the catheter adapter 14. In some embodiments, the pressure may correspond to the high pressure or greater than or equal to 300 psi. In some embodiments, prior to the pressure being applied to the septum 12, the outer margin 48 of the washer 44 may contact the wall 28 of the catheter adapter 14, but a force exerted by the washer 44 on the wall 28 of the catheter adapter 14 may be nominal or low. In some embodiments, the nominal or low pressure may increase a shelf-life of the catheter assembly 43.

In some embodiments, prior to the pressure being applied to the septum 12, the washer 44 may contact the septum 12 or a space may be disposed between the septum 12 and the washer 34. In some embodiments, in response to the pressure being applied to the septum 12, the septum 12 may contact and/or apply pressure to the washer 44 in a proximal direction, which may cause the washer 44 to compress or flatten in a stressed state. When the washer 44 compresses, the washer 44 may lose some or all of its conical or dome shape. In some embodiments, the compression may or may not be visible to the naked eye. In some embodiments, compressing the washer 44 may increase a diameter of the washer 44 and cause the washer 44 to exert a greater force on the wall 28 of the catheter adapter 14, resulting in the washer 44 being held more securely within the catheter adapter 14 when the pressure is applied to the septum 12.

In some embodiments, the washer 34 may be spring-like or resilient. In some embodiments, when the pressure is no longer applied to the septum 12, the washer 34 may automatically return to an original conical or dome shape and apply less force to the wall 28 of the catheter adapter 14. Suitable materials for the washer 44 may include, but are not limited to, thermoplastic polymeric resins such as polycarbonate, polystyrene, polypropylene, polycarbonate, polyethylene terephthalate glycol (PETG), copolyester, and the like. Suitable materials for the washer 44 may include, but are not limited to, metals such as steel, zinc, nickel, silver, and the like.

In some embodiments, the outer margin 48 of the washer 44 may include one or more inwardly-extending slots 54. Additionally or alternatively, in some embodiments, the inner margin 46 of the washer 44 may include one or more outwardly-extending slots 56. In some embodiments, the slots 54 and/or the slots 56 may facilitate compression or flattening of the washer 44 in response to the septum 12 applying force to the dome shape of the washer 44. When the washer 44 is compressed, the inner margin 46 may move closed to the outer margin 48. In some embodiments, the washer 44 may secure the septum 12 within the lumen 30 of the catheter adapter 14 in response to increased pressure, due to, for example, infusion, without use of adhesive, welding, or other securement mechanisms.

In some embodiments, the inner margin 46 may define an aperture 59 of the washer 44, which may be centrally located and through which the introducer needle 40 may extend when the catheter assembly 43 is in the insertion configuration. In some embodiments, an outer diameter of the needle 40 may be less than a diameter of the inner margin 46.

Figure 3A:
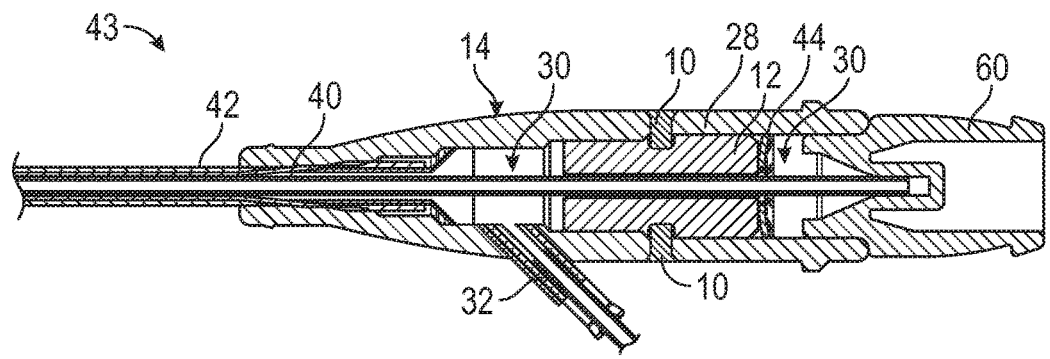
FIG. 3A is a cross-sectional top view of another catheter assembly, illustrating the catheter assembly in an insertion configuration, according to some embodiments.
Figure 3B:
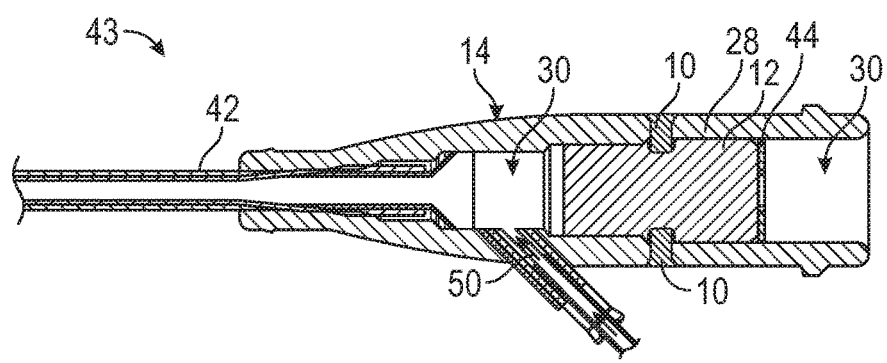
FIG. 3B is a cross-sectional top view of the catheter assembly of FIG. 3A, illustrating the catheter assembly in a fluid delivery configuration, according to some embodiments.
Figure 3C:
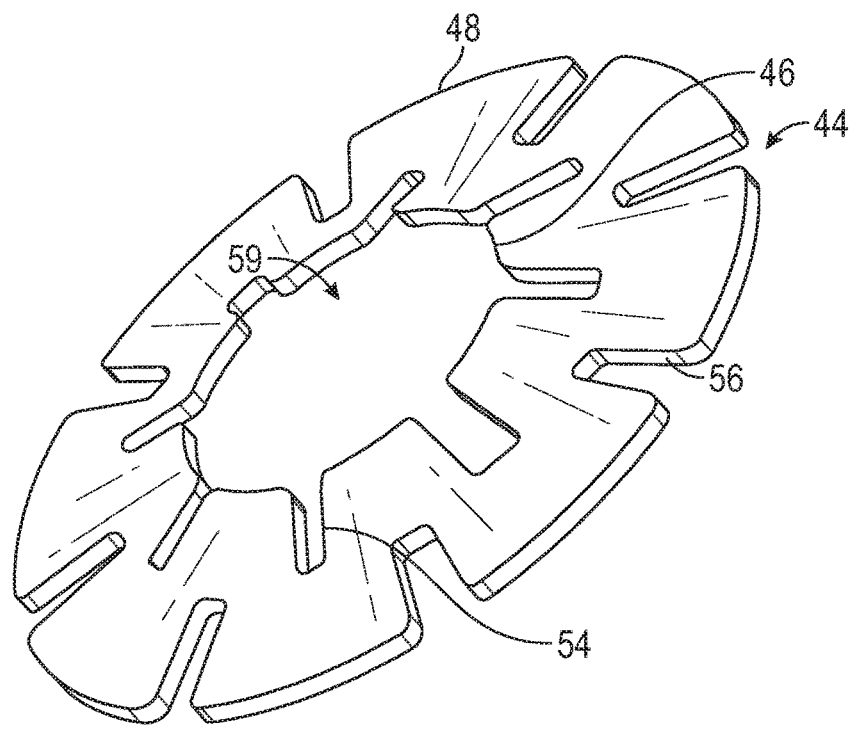
FIG. 3C is an upper perspective view of an example washer which may be included in the catheter assembly of FIG. 3A, according to some embodiments.
Figure 3D:
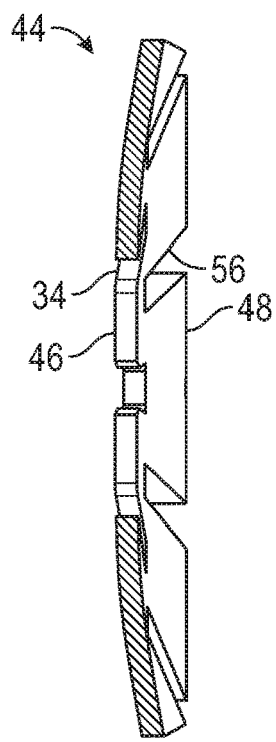
FIG. 3D is a cross-sectional side view of the washer of FIG. 3C, according to some embodiments.

An example relaxed state of the washer 44 is illustrated in FIG. 3A and FIGS. 3C-3D. An example stressed state of the washer 44 is illustrated in FIG. 3B. In some embodiments, the washer 44 may be disposed in the relaxed state when the catheter assembly 43 is in the insertion configuration. In some embodiments, the washer 44 may be disposed in the stressed state when a needle assembly 60 is removed, the catheter assembly 43 is in the fluid delivery configuration, and fluid flows into the catheter adapter 14, exerting a proximal force on the septum 12. In some embodiments, the fluid 50 may force the septum 12 proximally against the washer 44. In some embodiments, the inner margin 46 may move toward the outer margin 48 in response to the septum being forced proximally against the washer 44, and the outer margin 48 may remain stationary and in contact with the wall 28.

Figure 3E:
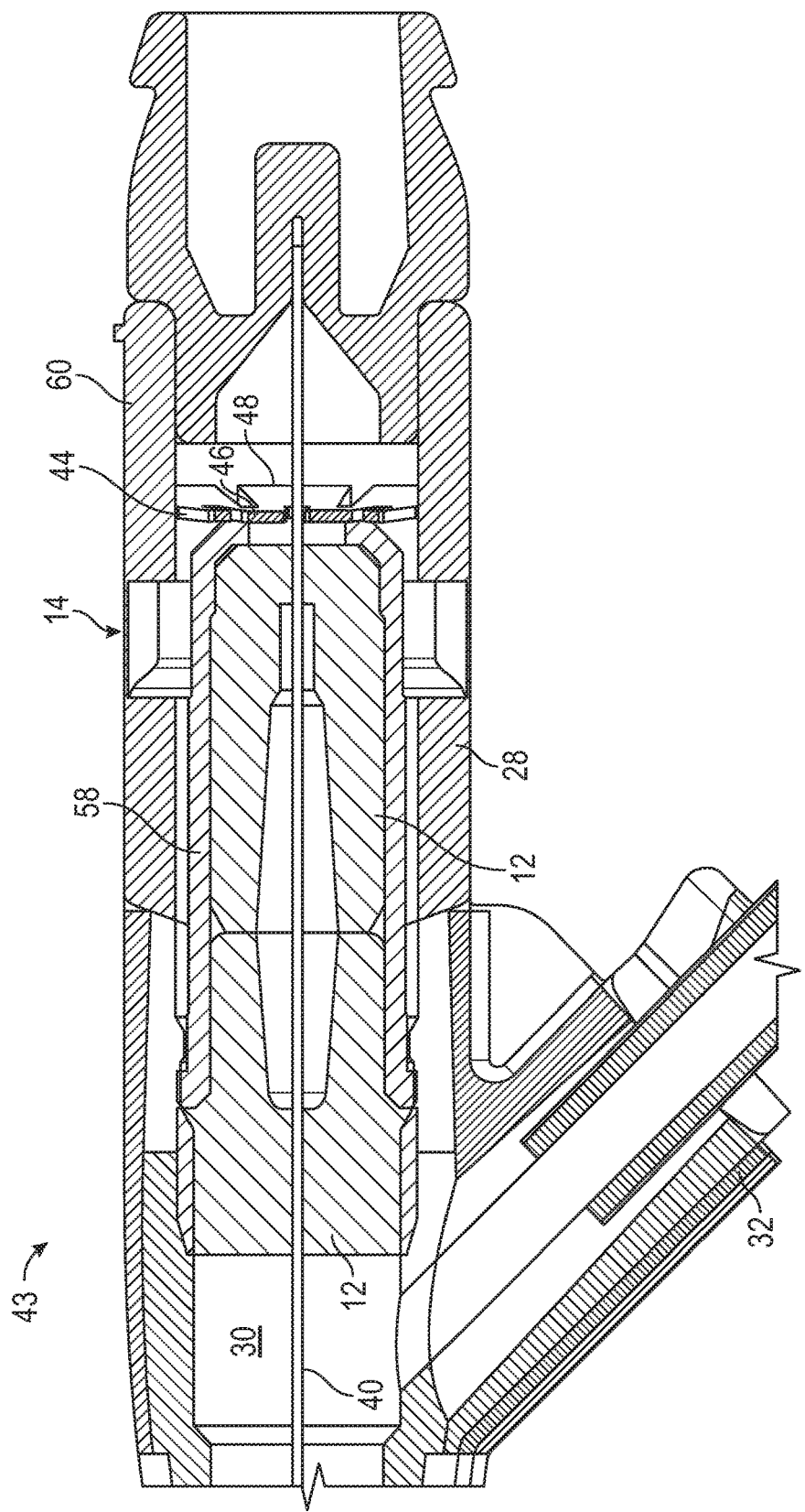
FIG. 3E is a cross-sectional top view of the catheter assembly of FIG. 3A, illustrating the catheter assembly in the insertion configuration and an example canister, according to some embodiments.
Figure 3F:
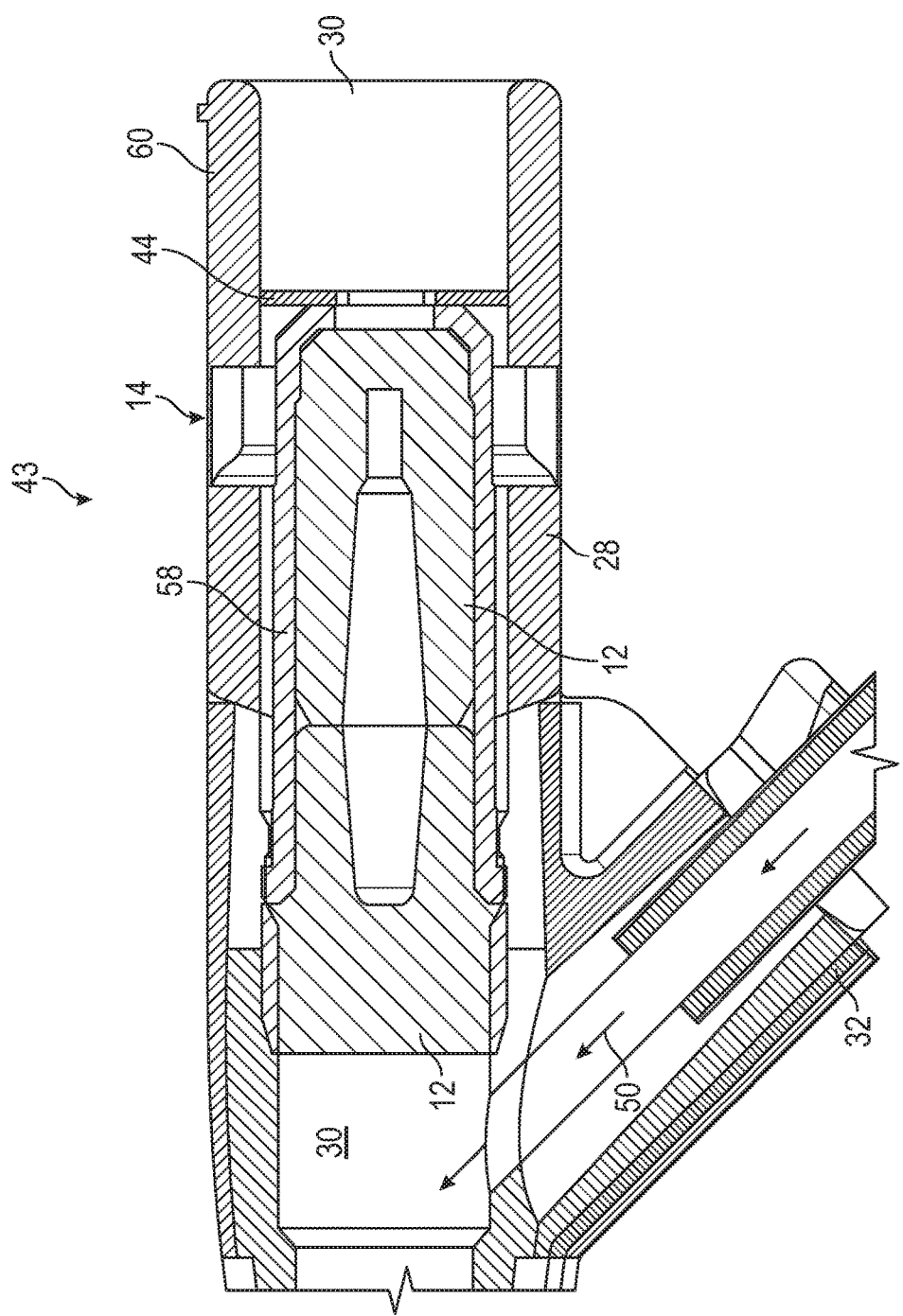
FIG. 3F is a cross-sectional top view of the catheter assembly of FIG. 3A, illustrating the catheter assembly in the fluid delivery configuration and the canister of FIG. 3E, according to some embodiments.

The catheter assembly 43 may include any suitable type of septum 12. Referring now to FIGS. 3E-3F, in some embodiments, the septum 12 may be disposed in a holder or canister 58, which may contact and apply a proximal force to the washer 44 to compress the washer 44, similar to the septum 12 as discussed with respect to FIGS. 3A-3D. In some embodiments, the canister 58 may contact and apply a proximal force to the washer 34, similar to the septum 12 as discussed with respect to FIGS. 2A-2D. In some embodiments, the septum 12 may include a low-drag septum 12. In some embodiments, the septum stoppers 10 may extend through the wall 28 and into or through the canister 58, similar to as disclosed with respect to FIGS. 1A-1D.

Figure 4A:
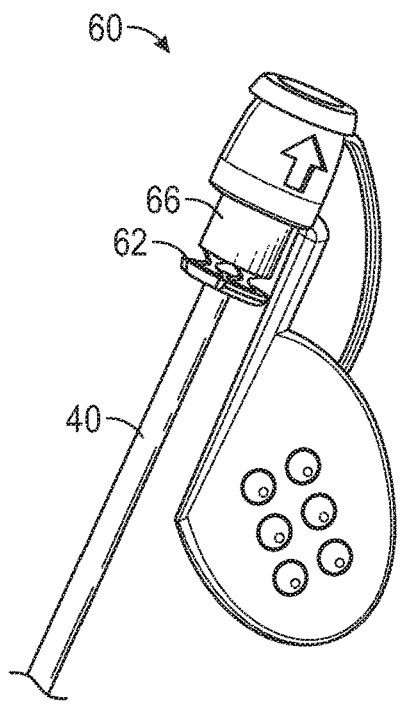
FIG. 4A is an upper perspective view of an example needle assembly and example retention disc, according to some embodiments.
Figure 4B:
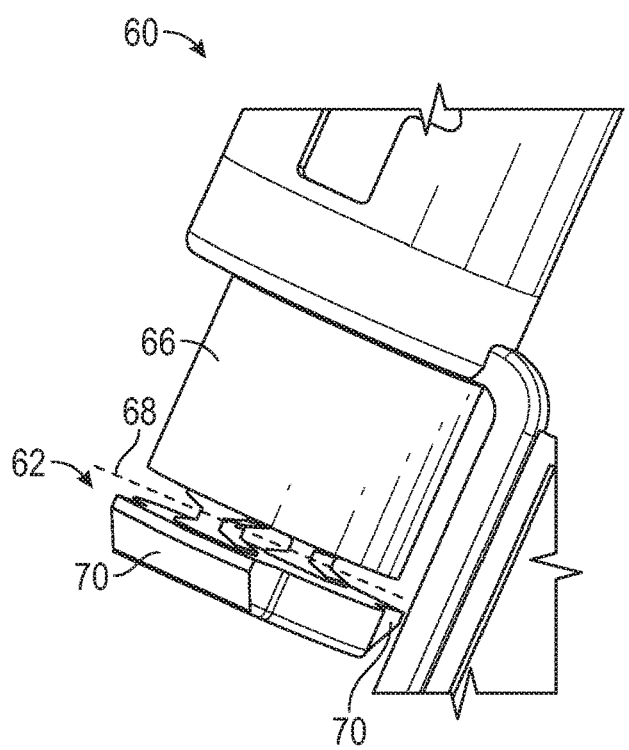
FIG. 4B is an enlarged upper perspective view of a portion of the needle assembly and retention disc of FIG. 4A, according to some embodiments.

Referring now to FIGS. 4A-4B, in some embodiments, a proximal end of the needle assembly 60 of a catheter assembly 61 may include a retention disc 62, which may be configured to secure the septum 12 disposed within the catheter adapter 14. In some embodiments, the catheter assembly 61 may include or correspond to one or more of the following: the catheter assembly 16 of FIG. 1, the catheter assembly 33 of FIG. 2, or the catheter assembly 43 of FIG. 3. In some embodiments, the retention disc 62 may be connected to a portion of the needle assembly 60 by one or more breakable arms 64. In some embodiments, the portion of the needle assembly 60 may include a needle hub 66 of the needle assembly 60. In other words, the arms 64 may extend between the retention disc 62 and the needle hub 66. In some embodiments, a proximal end of the needle 40 may be secured within the needle hub 66.

In some embodiments, any number of arms 64 may extend between the retention disc 62 and the portion of the needle assembly 60. In some embodiments, a first arm 64a and a second arm 64b (which may be referred to in the present disclosure as "arms") may be disposed on opposite sides of the needle assembly 60. In some embodiments, the needle assembly 60 may be molded with a line of weakness 68 extending through the arms 64. In some embodiments, the line of weakness 68 may include indented or thinner portions of the arms 64.

In some embodiments, the retention disc 62 may include a coupling mechanism for coupling the retention disc 62 to the wall 28 of the catheter adapter 14. The coupling mechanism may include any suitable coupling mechanism. For example, the retention disc 62 may include one or more wings 70, which may be sized and configured to snap into or interfere with a corresponding groove or opening 72 in the wall 28. In some embodiments, the retention disc 62 may include a first wing 70a and a second wing 70b. As another example, the retention disc 62 may include one or more threads that may correspond to one or more threads of the wall 28 of the catheter adapter 14.

Figure 4C:
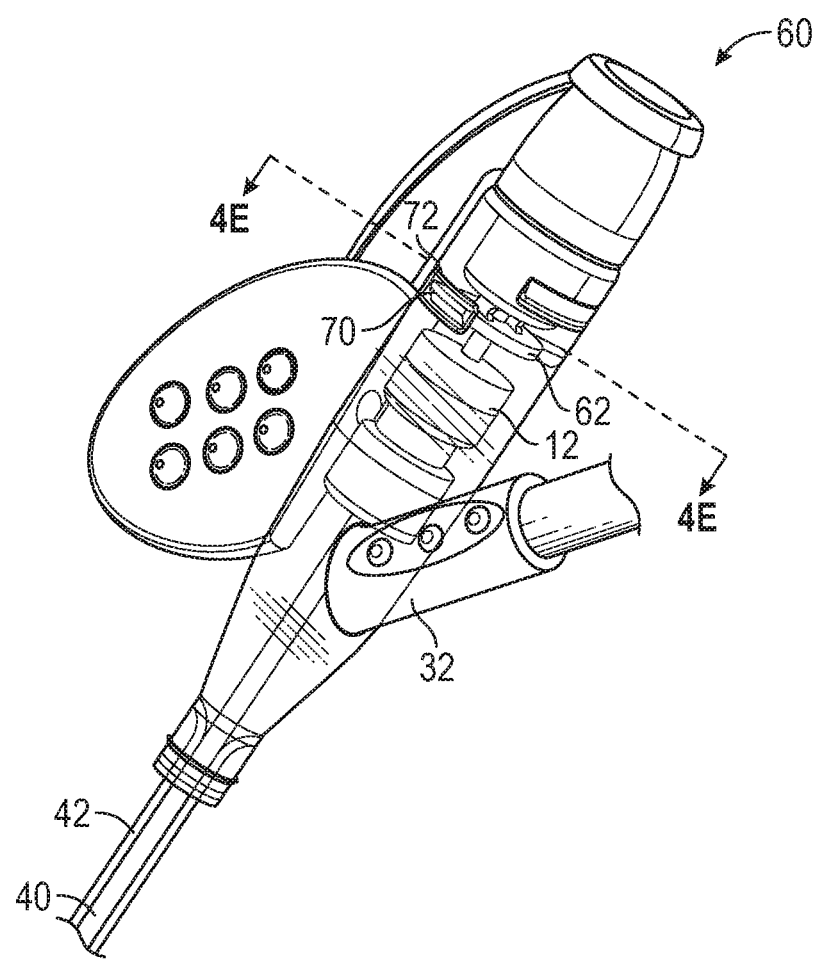
FIG. 4C is an upper perspective view of another catheter assembly, illustrating the needle assembly of FIG. 4A secured via the retention disc, according to some embodiments.

Referring now to FIG. 4C, in some embodiments, the needle assembly 60 and the retention disc 62 may be inserted into a proximal end of the catheter adapter 14 and coupled to the catheter adapter 14 via the coupling mechanism. For example, the needle assembly 60 may be inserted into a proximal end of the catheter adapter 14 such that the wings 70 of the retention disc 62 are aligned with the openings 72 or grooves in the wall 28. Thus, the retention disc 62 and the needle assembly 60 may be secured within the catheter adapter 14.

In some embodiments, after the retention disc 62 is secured within the catheter adapter 14, a proximal portion of the needle assembly 60 may be twisted or rotated with respect to the catheter adapter 14, which may cause the arms 64 to break along the line of weakness 68. In some embodiments, in response to the arms 64 breaking, the proximal portion of the needle assembly 60 may be separated from the catheter adapter 14 and the retention disc 62, which may remain secured to the catheter adapter 14.

In some embodiments, the retention disc 62 may retain or secure the septum 12 within the catheter adapter 14 in response to increased pressure, due to, for example, infusion. In some embodiments, the increased pressure may be 300 psi or greater. In some embodiments, the retention disc 62 may contact and/or apply pressure to a proximal end of the septum 12 or a canister 58 of the septum 12 in response to the increased pressure. Thus, the retention disc 62 may prevent the septum 12 from becoming dislodged or exiting a proximal end of the catheter adapter 14 in the fluid configuration.

Figure 4D:
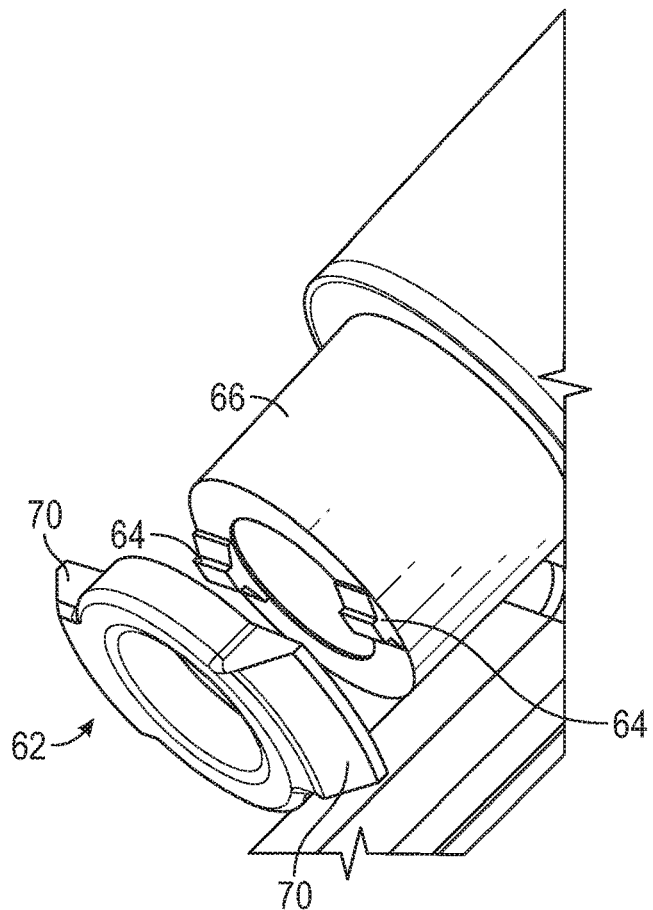
FIG. 4D is an enlarged lower perspective view of the retention disc of FIG. 4C separated from the needle assembly of FIG. 4A, according to some embodiments.
Figure 4E:
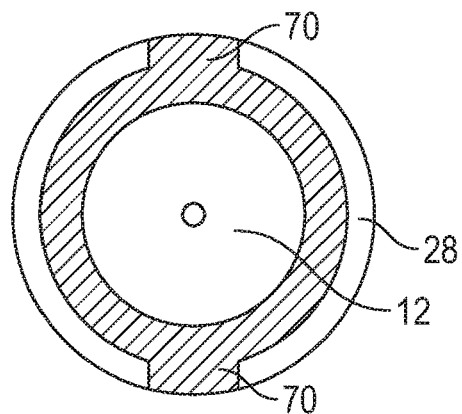
FIG. 4E is a cross-sectional view of the catheter assembly of FIG. 4C, across line 4E-4E of FIG. 4C, according to some embodiments.

FIG. 4D is an enlarged lower perspective view of the retention disc 62 separated from the proximal portion of the needle assembly 60, according to some embodiments, for illustrative purposes. FIG. 4E is a cross-sectional view of the catheter assembly 61, across line 4E-4E of FIG. 4C, according to some embodiments. FIG. 4E illustrates the catheter assembly 61 in the fluid delivery configuration, after the needle 40 has been withdrawn proximally through the septum 12. As illustrated in FIGS. 4D-4E, the retention disc 62 may be ring-shaped and/or include a central aperture through which the needle 40 may extend.

The present invention may be embodied in other specific forms without departing from its structures, methods, or other essential characteristics as broadly described herein and claimed hereinafter. The catheter assemblies discussed with respect to FIGS. 1-4 may include additional elements and/or components. The catheter assemblies discussed with respect to FIGS. 1-4 may include various types of needle safety mechanisms. It is understood that the septum stoppers 10, the washer 34, the washer 44, and the retention disc 62 may be used in various types of catheter assemblies, vascular access devices, and with various types of septa. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
 a catheter adapter, comprising a proximal end, a distal end, and a lumen extending therebetween, wherein the distal end comprises a catheter configured to be inserted into vasculature of a patient;
 a septum disposed within the lumen; and
 a septum securement element, wherein the septum securement element is disposed proximal to a distal end of the septum, wherein the septum securement element is configured to secure the septum in response to a proximal force on the septum, wherein the septum securement element comprises a septum stopper, wherein the septum stopper extends through a wall of the catheter adapter, wherein the septum stopper comprises a cylindrical bottom portion and a head, wherein the head has a greater diameter than the cylindrical bottom portion.

2. The catheter assembly of claim 1, wherein the septum stopper extends through a stopper hole in the wall of the catheter adapter, wherein the stopper hole includes an outer portion having a shape corresponding to the head and an inner portion having a shape corresponding to the cylindrical bottom portion.

3. The catheter assembly of claim 1, wherein the septum stopper is a first septum stopper, further comprising a second septum stopper, wherein in the first septum stopper and the second septum stopper oppose each other.

4. The catheter assembly of claim 1, wherein the septum comprises a groove, wherein the septum stopper extends through the wall of the catheter adapter into the groove of the septum, wherein the groove comprises an adhesive.

5. The catheter assembly of claim 4, wherein the groove of the septum is annular.

* * * * *